United States Patent [19]

Schuster et al.

[11] Patent Number: 4,607,123

[45] Date of Patent: Aug. 19, 1986

[54] WATER SOLUBLE 3,5-DIACETAMIDO-2,4,6-TRIIODOBENZOIC ACID DERIVATIVES

[75] Inventors: Dan-Karl Schuster, Mannheim; Franz J. Köhler, Alsbach-Hähnlein, both of Fed. Rep. of Germany

[73] Assignee: Dr. Franz Köhler Chemie GmbH, Alsbach-Hahnlein, Fed. Rep. of Germany

[21] Appl. No.: 700,631

[22] Filed: Feb. 12, 1985

[30] Foreign Application Priority Data

Feb. 29, 1984 [DE] Fed. Rep. of Germany ....... 3407473

[51] Int. Cl.$^4$ .................... C07C 103/50; A61K 49/04
[52] U.S. Cl. ........................................ 564/153; 424/5
[58] Field of Search .................. 564/153; 562/456; 424/5

[56] References Cited

U.S. PATENT DOCUMENTS 3,701,771 10/1972 Almen et al. .................. 564/153 X
4,021,481 5/1977 Almen et al. ..................... 564/153
4,062,934 12/1977 Tilly et al. ...................... 564/153 X

FOREIGN PATENT DOCUMENTS 867880 5/1961 United Kingdom ................ 562/456

Primary Examiner—Bernard Helfin
Attorney, Agent, or Firm—Kane, Dalsimer, Kane, Sullivan and Kurucz

[57] ABSTRACT

The invention relates to novel water soluble 3,5-diacetamido-2,4,6-triiodobenzoic acid derivatives, the method for making the same and their use as X-ray contrast agents for vasography, urography, myelography, artrography, fistulography and salpingography.

10 Claims, No Drawings

WATER SOLUBLE 3,5-DIACETAMIDO-2,4,6-TRIIODOBENZOIC ACID DERIVATIVES

BACKGROUND OF THE INVENTION

1. Field of the Invention

The invention relates to novel non-ionic derivatives of 3,5-diacetamido-2,4,6-triiodobenzoic acids, the process of their preparation and use. The subject matter of the invention are novel, nonionic derivatives of 3,5-diacetamido-2,4,6-triiodobenzoic acid. They are characterized partially by their high solubility in water, by the electroneutrality of their water solutions, by a reduced osmotic pressure in comparison with the corresponding salts of the 3,5-diacetamido-2,4,6-triiodobenzoic acid, by acceptable viscosities for injection and by extremely low toxicity. The novel compounds of the invention are useful in X-ray contrast formulations as the active ingredient.

2. Brief Description of the Prior Art

Corresponding derivatives of glycine ester, methyl amino acetic ester and proline ester were previously described by H. Suter and H. Zutter in "Helv. Chim. Acta", 54 (1971), page 2551–2559. However, these derivatives are more complicated to synthesize than the compounds of the invention. Also, the prior kind compounds do not correspond to the structures of the compounds of the invention and are not non-ionic. Therefore, they belong to a completely different class of X-ray contrast agents.

SUMMARY OF THE INVENTION

The invention comprises compounds of the formula:

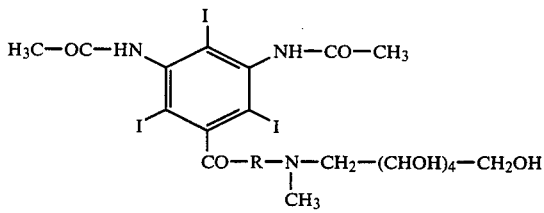

wherein R denotes an amino acid residue.

The compounds (I) of the invention are useful X-ray contrast agents.

DETAILED DESCRIPTION OF THE PREFERRED EMBODIMENTS OF THE INVENTION

Of the novel compounds of the formula (I) given above, there are certain preferred compounds, for use in X-ray contrast compositions.

Particularly preferred are compounds (I) wherein R denotes an alanine-, β-alanine-, sarcosine-, amino butyric acid-, leucine-, serine-, phenyl-alanine-, N-lactyl-lysine-, aspartic acid-, glutamic acid or like residue Preferred also are the specific compounds:
N,N-[(3,5-diacetamido-2,4,6-triiodobenzoyl)-sarcosine]-N-methyl glucamide (II);
N,N-[(3,5-diacetamido-2,4,6-triiodobenzoyl)-L-alanine]-N-methyl glucamide (III);
N,N-[(3,5-diacetamido-2,4,6-triiodobenzoyl)-β-alanine]-N-methyl glucamide (IV);
N,N-[(3,5-diacetamido-2,4,6-triiodobenzoyl)-γ-amino butyric acid]-N-methyl glucamide (V);
N,N-[(3,5-diacetamido-2,4,6-triiodobenzoyl)-L-leucine]-N-methyl glucamide (VI);
N,N-[(3,5-diacetamido-2,4,6-triiodobenzoyl)-L-phenylalanine]-N-methyl glucamide (VII);
N,N-[(3,5-diacetamido-2,4,6-triiodobenzoyl)-L-serine]-N-methyl glucamide (VIII);
N,N-[(3,5-diacetamido-2,4,6-triiodobenzoyl)-L-aspartic acid]-bis-N-methyl glucamide (IX);
N,N-[(3,5-diacetamido-2,4,6-triiodobenzoyl)-DL-aspartic acid]-bis-N-methyl glucamide (X);
N,N-[(3,5-diacetamido-2,4,6-triiodobenzoyl)-L-glutamine acid]-bis-N-methyl glucamide (XI);
N,N-[α-lactyl-ε-(3,5-diacetamido-2,4,6-triiodobenzoyl)-lysine]-N-methyl-glucamide (XII);
N,N-[ε-lactyl-α-(3,5-diacetamido-2,4,6-triiodobenzoyl)-lysine]-N-methyl glucamide (XIII);
N-(3,5-diacetamido-2,4,6-triiodobenzoyl)-amino acid of the general formula (XV) given below, and -amino acid ester of the general (XIV) formula also given below, wherein R is an amino acid residue, R' a lower alkyl or ortho or p-nitrophenyl ester;
N-(3,5-diacetamido-2,4,6-triiodobenzoyl)-sarcosine (XVI), sarcosine ethyl ester (XVII), -sarcosine-o-nitrophenylester (XVIII);
N-(3,5-diacetamido-2,4,6-triiodobenzoyl)-L-alanine (XIX), -L-alanine ethyl ester (XX), -L-alanine-o-nitrophenyl ester (XXI);
N-(3,5-diacetamido-2,4,6-triiodobenzoyl)-β-alanine (XXII);
-β-alanine ethylester (XXIII), -β-alanine-o-nitrophenyl ester (XXIV);
N-(3,5-diacetamido-2,4,6-triiodobenzoyl)-γ-amino butyric acid (XXV), -γ-amino butyric acid ethyl ester (XXVI), -γ-amino butyric acid-o-nitrophenyl ester (XXVII);
N-(3,5-diacetamido-2,4,6-triiodobenzoyl)-L-leucine (XXVIII), -L-leucine ethyl ester (XXIX), -L-leucine-o-nitrophenyl ester (XXX);
N-(3,5-diacetamido-2,4,6-triiodobenzoyl)-L-serine (XXXI), -L-serine ethyl ester (XXXII), -L-serine-o-nitrophenyl ester (XXXIII);
N-(3,5-diacetamido-2,4,6-triiodobenzoyl)-L-phenylalanine (XXXIV), -L-phenylalanine ethyl ester (XXXV), -L-phenylalanine-o-nitrophenyl ester (XXXVI);
N-(3,5-diacetamido-2,4,6-triiodobenzoyl)-L-glutamic acid (XXXVII), -L-glutamic acid diethyl ester (XXXVIII);
N-[α-(0-acetyl-lactyl)-ε-(3,5-diacetamido-2,4,6-triiodobenzoyl)]-L-lysine ethyl ester (XXXIX);
N-[ε-(0-acetyl-lactyl)-α-(3,5-diacetamido-2,4,6-triiodobenzoyl)]-L-lysine ethyl ester (XL);
N-[ε-benzyloxycarbonyl-α-(3,5-diacetamido-2,4,6-triiodobenzoyl)]-L-lysine ethyl ester (XLI); and
N-[ε-benzyloxycarbonyl-α-(0-acetyl-lactyl)]-L-lysine ethyl ester with the formula:

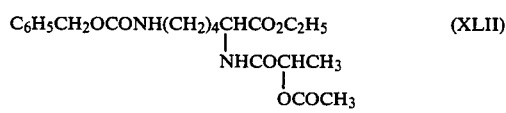

Particularly preferred are the compounds (II), (IX), (X) and (XI) described above.

The process for making the novel derivative compounds (I) of the invention is characterized in that an ester of the general formula:

(XIV)

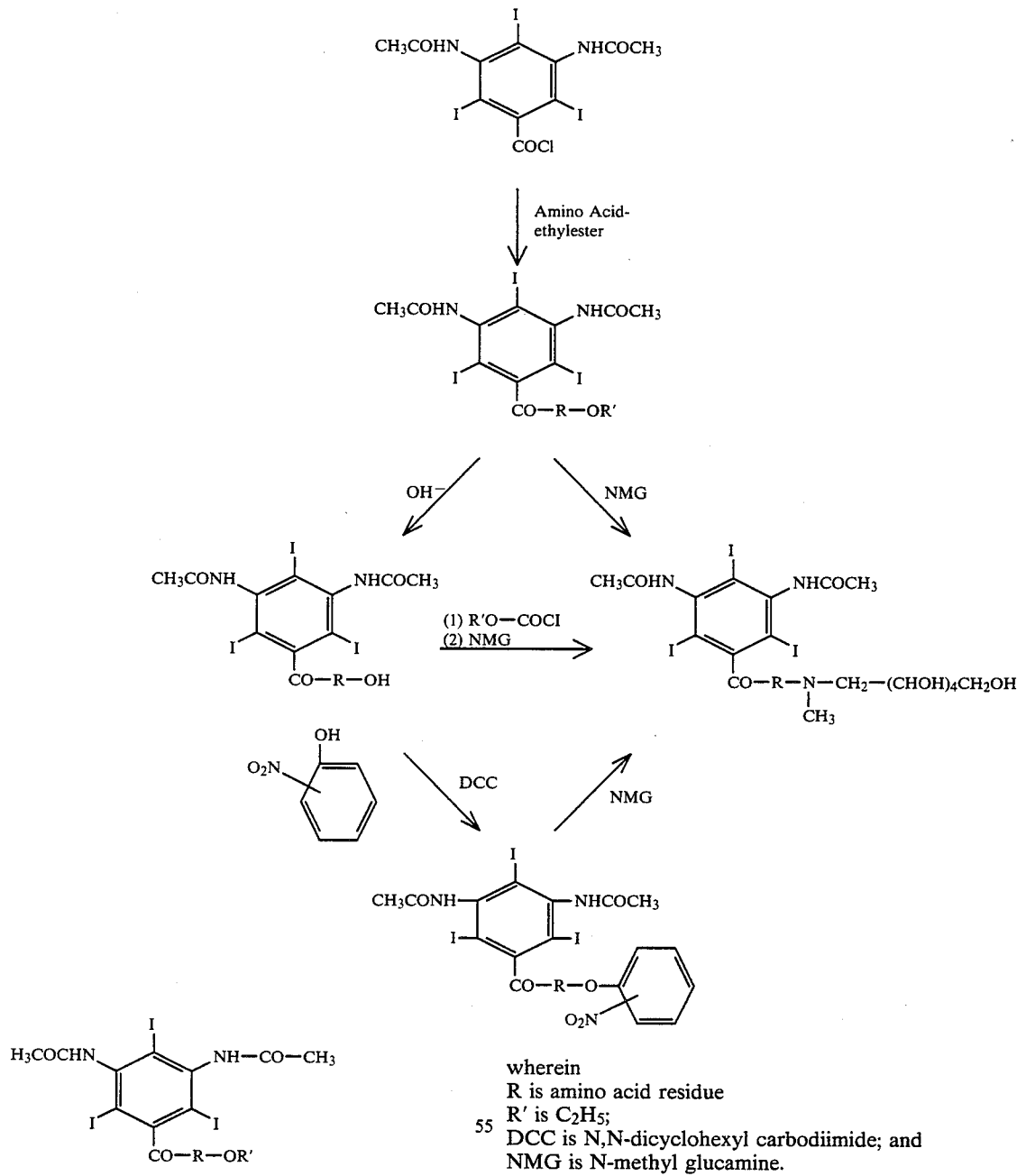

wherein R is an amino acid residue, R' an alkyl or ortho or p-nitrophenylester residue reacts with N-methyl glucamine in aprotic dipolar solvent, like N,N-dimethylformamide, N,N-dimethyl-acetamide or dimethylsulfoxide, in the presence of an alkali carbonate, for example at temperatures of 20° C.–80° C.

All compounds (I), with exception of the two lysine derivatives, are synthesized in accordance with the following schematic formulae:

wherein
R is amino acid residue
R' is $C_2H_5$;
DCC is N,N-dicyclohexyl carbodiimide; and
NMG is N-methyl glucamine.

The two lysine derivatives are synthesized according to the schematic formulae:

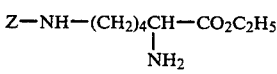

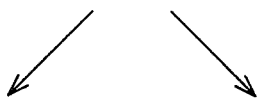

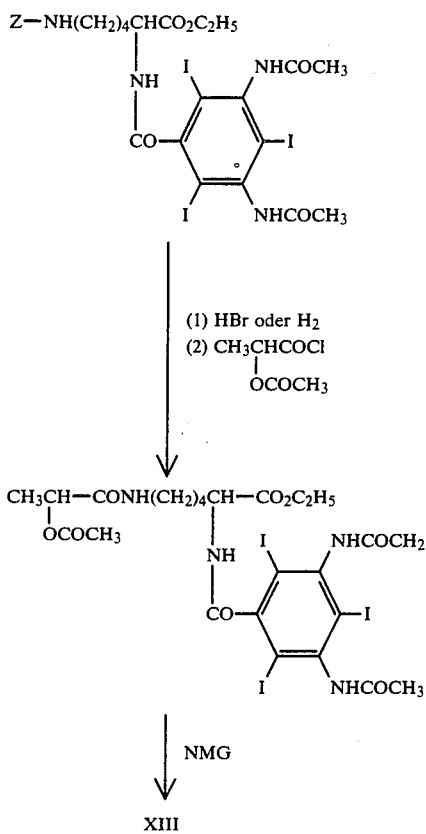
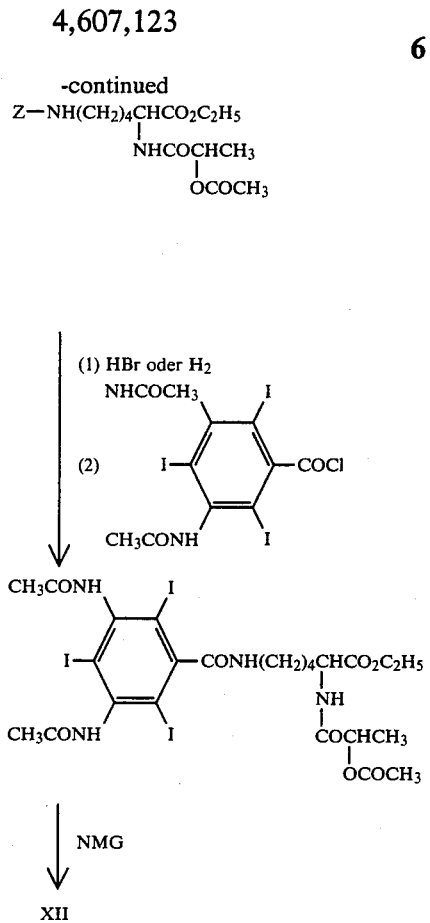

wherein
Z is C₆H₅CH₂OCO and
NMG is N-methyl glucamine.

The process for making the novel compounds of the general formula (I) is characterized in that a lower alkyl or nitrophenyl ester of the general formula XIV reacts with N-methyl glucamine in a aprotic solvent in the presence of alkali carbonate (in case of the nitrophenyl ester no alkali carbonate is necessary).

Preferably, N,N-dimethylformamide and N,N-dimethylacetamide are used as aprotic solvent. Advantageously, a potassium carbonate is used as the alkali carbonate.

The reaction temperature depends on the reactivity of the ester (XIV). Lower temperatures, for example, 20°–35° C. are optimum for the reactable o- or p-nitrophenyl ester, while higher temperatures, for example, 60°–80° C. are used for the lower alkyl esters (methyl, ethyl, propyl, etc.).

Advantageously, the reaction products are purified chromatographically. With suitable solubility conditions, for example, with β-alanine or γ-amino butyric acid-derivatives, the purification may also be performed by means of a simple recrystallisation.

Another process for making the compositions of the formula (I) is characterized in that N-(3,5-diacetamido-2,4,6-triiodobenzyl)-amino acids of the general formula (XV) react with an alkyl ester of the chloroformic acid in an aprotic dipolar solvent in the presence of a tertiary amine at temperatures of −15° C. to 0° C. Subsequently, the resulting anhydride reacts with N-methyl glucamine in a suitable solvent, like N,N-dimethylformamide, N,N-dimethylacetamide, ethanol or water at temperatures of −10° to +35° C. Ethyl- or isobutyl ester are preferred as esters of the chloroformic acid.

N,N-dimethylacetamide or N,N-dimethylformamide are advantageously used as aprotic dipolar solvents.

The most important side products of this process is the base substance which is generated by a wrong separation of the anhydride.

N-(3,5-diacetamido-2,4,6-triiodobenzoyl)-amino acid ethyl esters of the general formula (XIV) are synthesized by reaction of 3,5-diacetamido-2,4,6-triiodobenzoyl chloride with amino acid ethyl esters in N,N-dimethylformamide or N,N-dimethylacetamide in the presence of a tertiary amine at temperatures of 20°–60° C.

This general process also relates to the synthesis of N-(3,5-diacetamido-2,4,6-triiodobenzoyl)-L-aspartic acid diethyl ester (XLIII) and -DL-aspartic acid ethyl ester (XLIV), although both substances were already synthesized by a completely different process in 1963 (Daiischi Seiyaku Co., Ltd., Japan 19, 101 ('65), Aug. 27, Appl. Sept. 23, 1963; Chemical Abstracts 63, 18260 a, (1965).

Triethylamine, tributylamine or pyridine are preferred as tertiary amines. N-(3,5-diacetamido-2,4,6-triiodobenzoyl)-amino acid of the general formula (XV) are synthesized by the alkali saponification of the corresponding ester (XIV).

This process was also performed with the synthesis of N-(3,5-diacetamido-2,4,6-triiodobenzoyl)-L-aspartic acid (XLV) and -DL-aspartic acid (XLVI).

N-(3,5-diacetamido-2,4,6-triiodobenzoyl)-amino acid-o-(or p-)-nitrophenylester of the general formula (XIV) are synthesized by reacting N-(3,5-diacetamido-2,4,6-triiodobenzoyl)-amino acids with o-(or p-)-nitrophenol in N,N-dimethylformamide-tetrahydrofuran mixture in the presence of a coupling agent at temperatures of 0° to +30° C. N,N'-dicyclohexylcarbodiimide is preferred as a coupling agent.

The two lysine derivatives are synthesized in the following manner: ε,N-benzyloxycarbonyl-lysine ethyl ester reacts with 3,5-diacetamido-2,4,6-triiodobenzoyl chloride or o-acetyl-lactyl chloride in N,N-dimethylformamide or N,N-dimethylacetamide in the presence of a tertiary amine at temperatures of 20°–60° C. Triethylamine or tributylamine is preferred as a tertiary amine.

The protective group of N-[ε-benzyloxycarbonyl-α-(3,5-diacetamido-2,4,6-triiodobenzoyl)]-lysine ethyl ester or N-[ε-benzyloxycarbonyl-α-0-acetyllactyl]-lysine ethyl ester is removed with hydrobromic acid in acetic acid or with hydrogen (catalyst palladium on charcoal). Subsequently, α,N-(3,5-diacetamido-2,4,6-triiodobenzoyl)-lysine ethyl ester or α,N-(0-acetyl-lactyl)-lysine ethyl ester reacts with o-acetyl-lactyl chloride or with 3,5-diacetamido-2,4,6-triiodobenzoyl chloride in N,N-dimethylformamide or N,N-dimethylacetamide in the presence of a tertiary amine (triethyl- or tributylamine) at temperatures of 20°–60° C.

The following examples show the manner and the process of making and using the invention and set forth the best mode contemplated by the inventor of carrying out the invention but are not to be construed as limiting.

EXAMPLE 1

N,N-[(3,5-diacetamido-2,4,6-triiodobenzoyl)-sarcosine]-N-methyl glucamide (II)

(a) 2672 g (3.75 Mol) N-(3,5-diacetamido-2,4,6-triiodobenzoyl)-sarcosine ethyl ester, 1096 g (5.91 Mol) N-methyl-glucamine and 264 g (1.91 Mol) potassium carbonate in 6000 ml N,N-dimethylformamide were stirred for 24 hrs. at 60° C. (The reaction was monitored chromatographically; TLC-silicagel 60° F.$_{254}$ n-butanol-acetic acid-water 4:1:1). The reaction mixture was cooled to room temperature, filtered and the residue was washed with N,N-dimethylformamide, the solvent was evaporated under vacuum in a rotary evaporator. The residue was dissolved in water and the solution stirred with a cation exchanger and then with an anion exchanger, the aqueous solution was concentrated under vacuum in a rotary evaporator and was purified through a chromatographic colomne (Dowex 50 WX2, 100–200 mesh, H$^+$-form, elution agent: water). The selected fractions were neutralized with an anion exchanger, stirred with charcoal, filtered, reduced under vacuum in a rotary evaporator, well dried with methanol and benzol. The product was dissolved in N,N-dimethylformamide and precipitated with ethyl acetate, filtered and then washed with ethyl acetate and later with petroleum ether, dried over phosphorous pentoxide at 70° C. in the vacuum drying chamber and then over paraffin at room temperature. Yield: 1550 g (48%).

Analysis: $C_{21}H_{29}N_4O_9I_3$ (862.19): Calculated: C, 29.23%; H, 3.36%; N, 6.50%. Found: C, 29.27%; H, 3.52%; N, 6.77%.

$\lambda_{Max.}^{H2O}$ (log ε): 240 nm (4.48).

Thin layer chromatography TLC silica gel F$_{254}$ (Merck); System: n-butanolacetic acid-water 4:1:1) R$_f$=0.25; 0.33.

(b) In a solution of 6.85 g (10 mMol) N-(3,5-diacetamido-2,4,6-triiodobenzoyl)-sarcosine in 15 ml N,N-dimethylformamide which was cooled to −10° to −15° C., 1.6 ml (11.6 mMol) triethylamine and then 1,1 ml (11.6 mMol) ethyl chloroformate were added. After 5 minutes at −10° to −15° C. the triethyl ammonium chloride is filtered and the anhydride-solution is added dropwise to a suspension of 2.15 g (12 mMol) N-methyl glucamine in 10 ml N,N-dimethylformamide which was cooled to −10° C. The reaction mixture is immediately heated to room temperature, thereafter the reaction mixture is added dropwise to 250 ml ethyl acetate and stirred over night at room temperature. The precipitate is filtered, washed with ethyl acetate and then with petroleum ether and dried. The crude product is dissolved in water and is purified with a cation exchanger, anion exchanger and charcoal. The colorless, aqueous solution is reduced under vacuum, azeotropically dried, dissolved in 15 ml N,N-dimethylformamide and precipitated with 150 ml ethyl acetate. The product is filtered, washed and dried. Yield: 5–5.5 g (about 60%).

(c) 5.7 g (6.7 mMol) N-(3,5-diacetamido-2,4,6-triiodobenzoyl)-sarcosine-o-nitrophenyl ester and 1.2 g (6.2 mMol) N-methyl glucamine in 15 ml N,N-dimethylformamide are stirred for 24 hrs. at room temperature. The reaction mixture is added dropwise to 150 ml ethyl acetate, the precipitate is filtered, well washed with ethyl acetate, dissolved in water, adjusted to a pH of 3.5, purified with charcoal, then with a cation exchanger and an anion exchanger as aforementioned and finally dried. Yield: 2.7 g (about 50%).

EXAMPLE 2

N,N-[(3,5-diacetamido-2,4,6-triiodobenzoyl)-L-alanine]-N-methyl glucamide (III)

From 48 g (0.067 Mol) N-(3,5-diacetamido-2,4,6-triiodobenzoyl)-L-alanine ethyl ester, 19.6 g (0.1 Mol) N-methyl glucamine, 4.7 g (0.034 Mol) potassium carbonate and 480 ml N,N-dimethylformamide, about 35 g (61%) of the product was obtained following the procedure of example 1 a.

Analysis: $C_{21}H_{29}N_4O_9I_3$ (862.19): Calculated: C, 29.25%; H, 3.39%; N, 6.50%. Found: C, 29.32%; H, 3.61%; N, 6.65%.

$\lambda_{Max.}^{H2O}$ (log ε): 238 (4.49).

TLC silica gel; System (as above) R$_f$=0.33.

EXAMPLE 3

N,N-[(3,5-diacetamido-2,4,6-triiodobenzoyl)-β-alanine]-N-methyl glucamide (IV)

Following the procedure of example 1 a, 14.8 g (43%) of the desired compound was synthesized from 28.5 g (0.04 Mol) N-(3,5-diacetamido-2,4,6-triiodobenzoyl)-β-alanine ethyl ester, 11.7 g (0.06 Mol) N-methyl glucamine and 2.75 g (0.02 Mol) potassium carbonate in 285 ml N,N-dimethylformamide. This product can be recrystallized from methanol.

Analysis: $C_{21}H_{29}N_4O_9I_3$ (862.19): Calculated: C, 29.25%; H, 3.39%; N, 6.50%. Found: C, 29.57%; H, 3.90%, N, 6.56%.

$\lambda_{Max.}^{H2O}$ (log ε): 238 (4.47).

TLC silica gel, System (as above), R$_f$=0.29.

EXAMPLE 4

N,N-[(3,5-diacetamido-2,4,6-triiodobenzoyl)-γ-amino butyric acid]-N-methyl glucamide (V)

16.8 g (67%) of the desired compound is obtained from 20.7 g (0.028 Mol) N-(3,5-diacetamido-2,4,6-triiodobenzoyl)-γ-amino butyric acid ethyl ester, 8.2 g (0.042 Mol) N-methyl glucamine, 2.2 g (0.016 Mol) potassium carbonate and 145 ml N,N-dimethylformamide following the procedure of example 1 a. This compound could also be recrystallized from methanol.

Analysis: $C_{22}H_{31}N_4O_9I_3$ (876.22): Calculated: C, 30.16%; H, 3.57%; N, 6.39%. Found: C, 30.25%; H, 3.67%; N, 6.32%.

$\lambda_{Max}.^{H2O}$ (log ε): 247 (4.53).

TLC silica gel, System (as above), $R_f$=0.30.

EXAMPLE 5

N,N-[(3,5-diacetamido-2,4,6-triiodobenzoyl)-L-leucine]-N-methyl glucamide (VI)

Following the procedure of example 1 a, 31 g (54%) of the desired compound is obtained from 47.6 g (0.063 Mol) N-(3,5-diacetamido-2,4,6-triiodobenzoyl)-L-leucine ethyl ester, 19.5 g (0.1 Mol) N-methyl glucamine, 4.15 g (0.03 Mol) potassium carbonate and 475 ml N,N-dimethylformamide.

Analysis: $C_{24}H_{35}N_4O_9I_3$ (904.27): Calculated: C, 31.88%; H, 3.90%; N, 6.20%. Found: C, 31.66%; H, 4.31%; N, 5.94%.

$\lambda_{Max}.^{H2O}$ (log ε): 238 (4.36).

TLC silica gel, System (as above), $R_f$= −0.48.

EXAMPLE 6

N,N-[(3,5-diacetamido-2,4,6-triiodobenzoyl)-L-phenylalanine]-N-methyl glucamide (VII)

Following the procedure of example 1 a, 33 g (58%) of the product was obtained from 48 g (0.061 Mol) N-(3,5-diacetamido-2,4,6-triiodobenzoyl)-L-phenylalanine ethyl ester, 17.8 g (0.091 Mol) N-methyl glucamine and 4.2 g (0.032 Mol) potassium carbonate in 480 ml N,N-dimethylformamide.

Analysis: $C_{27}H_{33}N_4O_9I_3$ (938.29):

Calculated: C, 34.56%; H, 3.54%; N, 5.97%. Found: C, 35.49%; H, 3.89%; N, 5.76%.

$\lambda_{Max}.^{H2O}$ (log ε): 238 (4.45).

TLC silica gel, System (as above), $R_f$=0.49.

EXAMPLE 7

N,N-[(3,5-diacetamido-2,4,6-triiodobenzoyl)-L-serine]-N-methyl glucamide (VIII)

Following the procedure of example 1 a, 187 g (55%) of the desired compound is synthesized from 280 g (0.385 Mol) N-(3,5-diacetamido-2,4,6-triiodobenzoyl)-L-serine ethyl ester, 112 g (0.574 Mol) N-methyl glucamine, 26.5 g (0.192 Mol) potassium carbonate and 2800 ml N,N-dimethylformamide.

Analysis: $C_{21}H_{29}N_4O_{10}I_3$ (878.19): Calculated: C, 28.72%; H, 3.33%; N, 6.38%. Found: C, 29.38%; H, 3.55%; N, 6.65%.

$\lambda_{Max}.^{H2O}$ (log ε): 238 (4.46).

TLC silica gel, System (as above), $R_f$=0.26.

EXAMPLE 8

N,N-[(3,5-diacetamido-2,4,6-triiodobenzoyl)-L-aspartic acid]-bis-N-methyl glucamide (IX)

Following the procedure of example 1 a, 140 g (75%) of the product was made from 133 g (0.17 Mol) N-(3,5-diacetamido-2,4,6-triiodobenzoyl)-L-aspartic acid diethyl ester, 330 g (1.7 Mol) N-methyl glucamine and 25.5 g (0.185 Mol) potassium carbonate in 1300 ml N,N-dimethylformamide.

Analysis: $C_{29}H_{44}N_5O_{15}I_3$ (1083.40): Calculated: C, 32.15%; H, 4.09%; N, 6.46%. Found: C, 32.06%; H, 4.53%; N, 6.60%.

$\lambda_{max}.^{H2O}$ (log ε): 238 (4.44).

TLC silica gel, System (as above), $R_f$=0.09.

EXAMPLE 9

N,N-[(3,5-diacetamido-2,4,6-triiodobenzoyl)-DL-aspartic acid]-bis-N-methyl glucamide (X)

Following the procedure of example 1 a, 65.5 g (64%) of the product was synthesized from 70.5 g (0.09 Mol) N-(3,5-diacetamido-2,4,6-triiodobenzoyl)-DL-aspartic acid diethyl ester, 52.5 g (0.27 Mol) N-methyl glucamine, 6 g (0.043 Mol) potassium carbonate and 700 ml N,N-dimethylformamide.

Analysis: $C_{29}H_{44}N_5O_{15}I_3.3H_2O$ (1137.44): Calculated: C, 30.62%; H, 4.43%; N, 6.16%. Found: C, 29.92%; H, 4.66%; N, 6.34%.

$\lambda_{max}.^{H2O}$ (log ε): 238 (4.46).

TLC silica gel, System (as above) $R_f$=0.08.

EXAMPLE 10

N,N-[(3,5-diacetamido-2,4,6-triiodobenzoyl)-L-glutamic acid]-bis-N-methyl glucamide (XI)

Following the procedure of example 1 a, 12 g (70%) of the desired compound is obtained from 12.3 g (0.015 Mol) N-(3,5-diacetamido-2,4,6-triiodobenzoyl)-L-glutamic acid diethyl ester, 30 g (0.154 Mol) N-methyl glucamine, 2.35 g (0.017 Mol) potassium carbonate and 150 ml N,N-dimethylformamide.

Analysis: $C_{30}H_{46}N_5O_{15}I_3$ (1097.43): Calculated: C, 32.83%; H, 4.22%; N, 6.38%. Found: C, 33.61%; H, 4.72%; N, 6.47%.

$\lambda_{max}.^{H2O}$ (log ε): 238 (4.42).

TLC silica gel, System (as above), $R_f$=0.07.

EXAMPLE 11

N,N-[α-lactyl-ε-(3,5-diacetamido-2,4,6-triiodobenzoyl)-L-lysine]-N-methyl glucamide (XII)

Following the procedure of example 1 a, about 8 g (20%) of this substance is obtained from 37.8 g (0.425 Mol) N-[α-(0-acetyl-lactyl)-ε-(3,5-diacetamido-2,4,6-triiodobenzoyl]-L-lysine ethyl ester, 12.5 g (0.064 Mol) N-methyl glucamine and 3 g (0.0217 Mol) potassium carbonate.

Analysis: $C_{27}H_{40}N_5O_{11}I_3$ (991.35): Calculated: C, 32.71%; H, 4.07%; N, 7.07%. Found: C, 33.60%; H, 4.05%; N, 6.79%.

$\lambda_{max}.^{H2O}$ (log ε): 238 (4.47).

TLC silica gel, System (as above), $R_f$=0.33.

EXAMPLE 12

N,N-[ε-lactyl-α-(3,5-diacetamido-2,4,6-triiodobenzoyl)]-L-lysine-N-methyl-glucamide (XIII)

Following the procedure of example 1 a, about 7 g (29%) of the product was synthesized from 22.2 g (0.025 Mol) N-[ε-(0-acetyl-lactyl-α-(3,5-diacetamido-2,4,6-triiodobenzoyl)-L-lysine ethyl ester, 7.5 g (0.0385 Mol) N-methylglucamine and 1.8 g (0.013 Mol) potassium carbonate.

Analysis: $C_{27}40N_5O_{11}I_3$ (991.35): Calculated: C, 32.71%; H, 4.07%; N, 7.07%. Found: C, 33.60%; H, 4.30%; N, 7.12%.

$\lambda_{max}.^{H2O}$ (log ε): 238 (4.47).

TLC silica gel, System (as above), $R_f$=0.27.

EXAMPLE 13

N-(3,5-diacetamido-2,4,6-triiodobenzoyl)-sarcosine ethyl ester (XVII)

840 ml (6.1 Mol) triethylamine is added to a solution of 759 g (1.2 Mol) 3,5-diacetamido-2,4,6-triiodobenzoyl chloride and 276 g (1.8 Mol) sarcosine ethyl ester hydrochloride in 7600 ml N,N-dimethylformamide and stirred for 1 hr. at 60° C. The reaction mixture is cooled to room temperature, the crystallized triethyl ammonium chloride is filtered, washed with N,N-dimethylformamide and reduced under vacuum in a rotary evaporator. The residue is dissolved in 650 ml methanol and added dropwise to 3 l ethyl acetate. The precipitate is crystallized overnight, filtered to a dry state and finally washed with water, 1N hydrochloric acid, cold saturated sodium bicarbonate, water and dried under vacuum at 60° C. Yield: 685 g (80%).

Analysis: $C_{16}H_{18}N_3O_5I_3$ (713.05): Calculated: C, 26.95; H, 2.55%; N, 5.89%. Found: C, 26.69%; H, 2.40%; N, 5.70%.

EXAMPLE 14

N-(3,5-diacetamido-2,4,6-triiodobenzoyl)-L-alanine ethyl ester (XX)

Following the procedure of example 13, 50 g (70%) of the desired compound is recovered from 63.2 g (0.1 Mol) 3,5-diacetamido-2,4,6-triiodobenzoyl chloride and 23.1 g (0.15 Mol) L-alanine ethyl ester hydrochloride.

Analysis: $C_{16}18N_3O_5I_3$ (713.05): Calculated: C, 26.95%; H, 2.55%; N, 5.89%; Found: C, 27.62%; H, 2.56%; N, 5.87%.

EXAMPLE 15

N-(3,5-diacetamido-2,4,6-triiodobenzoyl)-β-alanine ethyl ester (XXIII)

Following the procedure of example 13, 53 g (75%) of the product is synthesized from 63.2 g (0.1 Mol) N-3,5-diacetamido-2,4,6-triiodobenzoyl chloride and 23.1 g (0.15 Mol) β-alanine ethyl ester hydrochloride.

Analysis: $C_{16}H_{18}N_3O_5I_3$ (713.05): Calculated: C, 26.95%; H, 2.55%; N, 5.89%. Found: C, 27.55%; H, 2.73%; N, 5.92%.

EXAMPLE 16

N-(3,5-diacetamido-2,4,6-triiodobenzoyl)-γ-amino butyric acid ethyl ester (XXVI)

Following the procedure of example 13, 15.5 g (71%) of the desired compound are obtained from 19.2 g (0.03 Mol) 3,5-diacetamido-2,4,6-triiodobenzoyl chloride and 7.5 g (0.045 Mol) γ-amino butyric acid ethyl ester hydrochloride.

Analysis: $C_{17}H_{20}N_3O_5I_3$ (727.07): Calculated: C, 28.08%; H, 2.77%; N, 5.80%. Found: C, 28.11%; H, 2.90%; N, 5.74%.

EXAMPLE 17

N-(3,5-diacetamido-2,4,6-triiodobenzoyl)-L-leucine ethyl ester (XXIX)

Following the procedure of example 13, 48 g (64%) of this product was synthesized from 63.2 g (0.1 Mol) 3,5-diacetamido-2,4,6-triiodobenzoyl chloride and 29.4 g (0.15 Mol) L-leucine ethyl ester hydrochloride.

Analysis: $C_{19}H_{24}N_3O_5I_3$ (755.03): Calculated: C, 30.21%; H, 3.20%; N, 5.56%. Found: C, 30.33%; H, 3.22%; N, 5.46%.

EXAMPLE 18

N-(3,5-diacetamido-2,4,6-triiodobenzoyl)-L-serine ethyl ester (XXXII)

Following the procedure of example 13, 281 g (82%) of the product was obtained from 295 g (0.47 Mol) 3,5-diacetamido-2,4,6-triiodobenzoyl chloride and 119 g (0.7 Mol) L-serine ethyl ester hydrochloride.

Analysis: $C_{16}H_{17}N_3O_6I_3$ (728.04): Calculated: C, 26.36%; H, 2.50%; N, 5.76%. Found: C, 25.90%; H, 2.27%; N, 5.65%.

EXAMPLE 19

N-(3,5-diacetamido-2,4,6-triiodobenzoyl)-L-phenylalanine ethyl ester (XXXV)

Following the procedure of example 13, 60 g (75%) of the product was synthesized from 63.2 g (0.1 Mol) 3,5-diacetamido-2,4,6-triiodobenzoyl chloride and 33.5 g (0.15 Mol) L-phenylalanine ethyl ester hydrochloride.

Analysis: $C_{22}H_{22}N_3O_5I_3$ (789.15): Calculated: C, 33.49%; H, 2.81%; N, 5.32%. Found: C, 33.75%; H, 2.83%; N, 5.29%.

EXAMPLE 20

N-(3,5-diacetamido-2,4,6-triiodobenzoyl)-L-aspartic acid diethyl ester (XLIII)

Following the procedure of example 13, 112 g (65%) of the product is synthesized from 140 g (0.22 Mol) 3,5-diacetamido-2,4,6-triiodobenzoyl chloride and 75 g (0.33 Mol) L-aspartic acid diethyl ester hydrochloride.

Analysis: $C_{19}H_{22}N_3O_7I_3$ (785.01): Calculated: C, 29.06%; H, 2.82%; N, 5.35%. Found: C, 29.44%; H, 2.86%; N, 5.11%.

EXAMPLE 21

N-(3,5-diacetamido-2,4,6-triiodobenzoyl)-DL-aspartic acid diethyl ester (XLIV)

Following the procedure of example 13, about 100 g (65%) of the desired compound are obtained from 127 g (0.2 Mol) 3,5-diacetamido-2,4,6-triiodobenzoyl chloride and 67.5 g (0.3 Mol) DL-aspartic acid diethyl ester hydrochloride.

Analysis: $C_{19}H_{22}N_3O_7I_3$ (785.01): Calculated: C, 29.06%; H, 2.82%; N, 5.35%. Found: C, 29.04%; H, 2.95%; N, 5.39%.

EXAMPLE 22

N-(3,5-diacetamido-2,4,6-triiodobenzoyl)-L-glutamic acid diethyl ester (XXXVIII)

Following the procedure of example 13, 155 g (65%) of product is synthesized from 192 g (0.3 Mol) 3,5-diacetamido-2,4,6-triiodobenzoyl chloride and 108 g (0.45 Mol) L-glutamic acid diethyl ester hydrochloride.

Analysis: $C_{20}H_{24}N_3O_7I_3$ (799.04): Calculated: C, 30.05%; H, 3.03%; N, 5.30%. Found: C, 30.11%; H, 3.02%; N, 5.32%.

EXAMPLE 23

N-(3,5-diacetamido-2,4,6-triiodobenzoyl)-sarcosine (XVI)

Into a suspension of 890 g (1.25 Mol) N-(3,5-diacetamido-2,4,6-triiodobenzoyl)-sarcosine ethyl ester in 3 l methanol cooled at 0° C., 1375 ml 1N sodium hydroxide is added dropwise at such a rate, that the temperature remains below +7° C. The solution is stirring 2 hours at 0° C. and overnight at roomtemperature, then acidified (pH 2.5; 6N HCl). The precipitate starts to separate. The mixture has to be stirred for a few more hours at roomtemperature and then a vigorous cooling down is performed (ice-salt mixture). The precipitate is filtered out, washed with some water and dried; Yield: 668 g (77%).

Analysis: $C_{14}H_{14}N_3O_5I_3.H_2O$ (703.01): Calculated: C, 23.92%; H, 2.29%; N, 5.98%. Found: C, 24.14%; H, 2.46%; N, 5.78%.

EXAMPLE 24

N-(3,5-diacetamido-2,4,6-triiodobenzoyl)-L-alanine (XIX)

Following the procedure of example 23, 65 g (92%) of this compound was synthesized from 71,3 g (0.1 Mol) N-(3,5-diacetamido-2,4,6-triiodobenzoyl)-L-alanine ethyl ester.

Analysis: $C_{14}H_{14}N_3O_5I_3.3H_2O$ (739.04): Calculated: C, 22.75%; H, 2.72%; N, 5.69%. Found: C, 22.74%; H, 2.05%; N, 5.71%.

EXAMPLE 25

N-(3,5-diacetamido-2,4,6-triiodobenzoyl)-β-alanine (XXII)

Following the procedure of example 23, 117 g (96%) of the product is made from 123 g (0.172 Mol) N-(3,5-diacetamido-2,4,6-triiodobenzoyl)-β-alanine ethyl ester.

Analysis: $C_{14}H_{14}N_3O_5I_3.H_2O$ (703.01): Calculated: C, 23.92%; H, 2.29%; N, 5.98%. Found: C, 23.09%; H, 1.96%; N, 5.89%.

EXAMPLE 26

N-(3,5-diacetamido-2,4,6-triiodobenzoyl)-γ-amino butyric acid (XXV)

Following the procedure of example 123, 119.7 g (95%) of the desired compound is synthesized from 125 g (0.172 Mol) N-(3,5-diacetamido-2,4,6-triiodobenzoyl)-γ-amino butyric acid ethyl ester.

Analysis: $C_{15}H_{16}N_3O_5I_3.2H_2O$ (735.05): Calculated: C, 24.51%; H, 2.74%; N, 5.72%. Found: C, 24.69%; H, 2.57%; N, 5.74%.

EXAMPLE 27

N-(3,5-diacetamido-2,4,6-triiodobenzoyl)-L-leucine (XXVIII)

Following the procedure of example 23, 62 g (85%) of this compound is obtained from 75.5 g (0.1 Mol) N-(3,5-diacetamido-2,4,6-triiodobenzoyl)-L-leucine ethyl ester.

Analysis: $C_{17}H_{20}N_3O_5I_3$ (727.07): Calculated: C, 28.08%; H, 2.77%; N, 5.78%. Found: C, 28.05%; H, 3.00%; N, 5.40%.

EXAMPLE 28

N-(3,5-diacetamido-2,4,6-triiodobenzoyl)-L-serine (XXXI)

Following the procedure of example 23, 56 g (80%) of the final product is synthesized from 72.8 g (0.1 Mol) N-(3,5-diacetamido-2,4,6-triiodobenzoyl)-L-serine ethyl ester.

Analysis: $C_{14}H_{14}N_3O_6I_3$ (700.99): Calculated: C, 23.99%; H, 2.01%; N, 5.99%. Found: C, 24.62%; H, 2.10%; N, 5.95%.

EXAMPLE 29

N-(3,5-diacetamido-2,4,6-triiodobenzoyl)-L-phenylalanine (XXXIV)

Following the procedure of example 23, 69 g (90%) of the desired compound is obtained from 79 g (0.1 Mol) N-(3,5-diacetamido-2,4,6-triiodobenzoyl)-L-phenylalanine ethyl ester.

Analysis: $C_{20}H_{18}N_3O_5I_3.H_2O$ (779.11): Calculated: C, 30.83%; H, 2.58%; N, 5.39%. Found: C, 30.64%; H, 2.12%; N, 5.39%.

EXAMPLE 30

N-(3,5-diacetamido-2,4,6-triiodobenzoyl)-L-aspartic acid (XLV)

Following the procedure of example 23, 455 g (80%) of the desired product is obtained from 618 g (0.787 Mol) N-(3,5-diacetamido-2,4,6-triiodobenzoyl)-L-aspartic acid diethyl ester.

Analysis: $C_{15}H_{14}N_3O_7I_3.2H_2O$ (765.03): Calculated: C, 23.55%; H, 2.37%; N, 5.49%. Found: C, 22.84%; H, 1.84%; N, 5.46%.

EXAMPLE 31

N-(3,5-diacetamido-2,4,6-triiodobenzoyl)-DL-aspartic acid (XLVI)

Following the procedure of example 23, 58 g (80%) of the compound is synthesized from 78.5 g (0.1 Mol) N-(3,5-diacetamido-2,4,6-triiodobenzoyl)-DL-aspartic acid diethyl ester.

Analysis: $C_{15}H_{14}N_3O_7I_3.3H_2O$ (783.04): Calculated: C, 23.01%; H, 2.57%; N, 5.37%. Found: C, 22.37%; H, 2.18%; N, 5.46%.

EXAMPLE 32

N-(3,5-diacetamido-2,4,6-triiodobenzoyl)-L-glutamic acid (XXXVII)

Following the procedure of example 23, 170.7 g (95%) of the desired compound is made from 192.6 g (0.24 Mol) N-(3,5-diacetamido-2,4,6-triiodobenzoyl)-L-glutamic acid diethyl ester.

Analysis: $C_{16}H_{16}N_3O_7I_3$ (743.03): Calculated: C, 25.86%; H, 2.17%; N, 5.65%. Found: C, 25.00%; H, 2.18%; N, 5.60%.

EXAMPLE 33

N-(3,5-diacetamido-2,4,6-triiodobenzoyl)-sarcosine-o-nitrophenyl ester (XVIII)

6.85 g (10 mMol) N-(3,5-diacetamido-2,4,6-triiodobenzoyl)-sarcosine and 1.7 g (12.2 mMol) o-nitrophenol are dissolved in 15 ml N,N-dimethylformamide. 60 ml tetrahydrofuran is added to this solution which is then cooled down to 0° C. 2,5 g (12 mMol) N,N-dicyclohexylcarbodiimide is added. The reaction runs for 2 hours at 0° C. and overnight at room temperature. The precipitate (N,N'-dicyclohexylurea) is filtered off, washed with 10 ml N,N-dimethylformamide, the tetrahydrofuran is distilled, the solution kept in the refrigerator overnight and then the dicyclohexylurea is again filtered off. The organic solution is added dropwise to 250 ml ether, the precipitate is decantered, dissolved with 25 ml N,N-dimethylformamide and added to water dropwise. The precipitate is filtered, washed with saturated sodium bicarbonate solution and water and dried. Yield: 5.4 g (67%).

Analysis: $C_{20}H_{17}N_4O_7I_3$ (806.09): Calculated: C, 29.80%; H, 2.13%; N, 6.95%. Found: C, 30.07%; H, 2.64%; N, 6.66%.

EXAMPLE 34

N-(3,5-diacetamido-2,4,6-triiodobenzoyl)-L-alanine-o-nitrophenyl ester (XXI)

Following the procedure of example 33, the desired compound is synthesized from 13.7 g (20 mMol) N-(3,5-diacetamido-2,4,6-triiodobenzoyl)-L-alanine, 3,5 g (25 mMol)-o-nitrophenol and 5 g (24 mMol) N,N'-dicyclohexylcarbodiimide.

Analysis: $C_{20}H_{17}N_4O_7I_3$ (806.09): Calculated: C, 29.80%; H, 2.13%; N, 6.95%. Found: C, 30.49%; H, 2.46%; N, 6.86%.

EXAMPLE 35

N-(3,5-diacetamido-2,4,6-triiodobenzoyl)-β-alanine-o-nitrophenyl ester (XXIV)

Following the procedure of example 33 the product is synthesized from 13.7 g (20 mMol) N-(3,5-diacetamido-2,4,6-triiodobenzoyl)-β-alanine, 3.5 g (25 mMol)-o-nitrophenol and 5 g (24 mMol) N,N'-dicyclohexylcarbodiimide. Yield 11 g (68%).

Analysis: $C_{20}H_{17}N_4O_7I_3$ (806.09): Calculated: C, 29.80%; H, 2.13%; N, 6.95%. Found: C, 30.73%; H, 2.41%; N, 6.79%.

EXAMPLE 36

N-(3,5-diacetamido-2,4,6-triiodobenzoyl)-γ-aminobutyric acid-o-nitrophenyl ester (XXVII)

Following the procedure of example 33, 8.5 g (52%) of product obtained from 14 g (20 mMol) N-(3,5-diacetamido-2,4,6-triiodobenzoyl)-γ-amino butyric acid, 3.5 g (25 mMol) o-nitrophenyl and 5 g (24 mMol) N,N'-dicyclohexylcarbodiimide.

Analysis: $C_{21}H_{19}N_4O_7I_3$ (820.12): Calculated: C, 30.76%; H, 2.34%; N, 6.83%. Found: C, 31.28%; H, 3.06%; N, 6.59%.

EXAMPLE 37

N-(3,5-diacetamido-2,4,6-triiodobenzoyl)-L-leucine-o-nitrophenyl ester (XXXIV)

Following the procedure of example 33, the product is synthesized from 14.6 g (20 mMol) N-(3,5-diacetamido-2,4,6-triiodobenzoyl)-L-leucine, 3,5 g (25 mMol) o-nitrophenol and 5 g (24 mMol) N,N'-dicyclohexylcarbodiimide. Yield: 12.5 g (73%).

Analysis: $C_{23}H_{23}N_4O_7I_3$ (848.17): Calculated: C, 32.57%; H, 2.73%; N, 6.61%. Found: C, 32.39%; H, 3.27%; N, 6.37%.

EXAMPLE 38

N-(3,5-diacetamido-2,4,6-triiodobenzoyl)-L-serine-o-nitrophenyl ester (XXXIII)

Following the procedure of example 33, about 8.5 g (52%) of the desired compound is synthesized from 14 g (20 mMol) N-(3,5-diacetamido-2,4,6-triiodobenzoyl)-L-serine, 3.5 g (25 mMol) O-nitrophenol and 5 g (24 mMol) N,N'-dicyclohexylcarbodiimide.

Analysis: $C_{20}H_{17}N_4O_8I_3$ (822.09): Calculated: C, 29.22%; H, 2.08%; N, 6.81%. Found: C, 30.14%; H, 2.27%; N, 6.86%.

EXAMPLE 39

N-(3,5-diacetamido-2,4,6-triiodobenzoyl)-L-phenylalanine-o-nitrophenyl ester (XXXVI)

Following the procedure of example 33, the desired product is obtained from 15.2 g (20 mMol) N-(3,5-diacetamido-2,4,6-triiodobenzoyl)-L-phenylalanine 3.5 g (25 mMol) O-nitrophenol and 5 g (24 mMol) N,N-dicyclohexylcarbodiimide.

Analysis: $C_{26}H_{21}N_4O_7I_3$ (882.19): Calculated: C, 35.40%; H, 2.40%; N, 6.35%. Found: C, 35.43%; H, 2.86%; N, 6.20%.

EXAMPLE 40

N-[ε-benzyloxycarbonyl-α-(3,5-diacetamido-2,4,6-triiodobenzoyl)]-L-lysine ethyl ester (XLI)

39 g (0.127 Mol) ε,N-benzyloxycarbonyl-L-lysine ethyl ester, 80.1 g (0.126 Mol) 3,5-diacetamido-2,4,6-triiodobenzoyl chloride and 26.5 ml (0.19 Mol) triethylamine are stirred for 24 Hrs. in 800 ml N,N-dimethylformamide at 60° C., thereafter the solvent is distilled off under vacuum, the residue is mixed with ethyl acetate, thereafter crystallized, the precipitate is filtered off, washed with petroleum ether, dried, washed with water, 1N hydrochloride acid, water, cold saturated sodium bicarbonate solution and water, and thereafter dried. Yield: 86 g (75%)

Analysis: $C_{27}H_{31}N_4O_7I_3$ (904.28): Calculated: C, 35.86%; H, 3.46%; N, 6.20%. Found: C, 36.05%; H, 3.41%; N, 6.19%.

EXAMPLE 41

N-[ε-benzyloxycarbonyl-α-(O-acetyl-lactyl)]-L-lysine ethyl ester (XLII)

43.3 g (0.14 Mol) ε,N-benzyloxycarbonyl-L-lysine ethyl ester and 30 ml (0.217 Mol) triethylamine are dissolved in 430 ml ethyl acetate and cooled to 0° C. 24 g (0.16 Mol) O-acetyl-lactyl chloride in 60 ml ethyl acetate are added dropwise at this temperature. The reaction last 2 hours at 0° C. and overnight at room temperature. The next day, the triethyl ammonium chloride is filtered, the organic solution is washed with water, then with saturated sodium bicarbonate solution and water, dried over sodium sulfate and the solvent is distilled off. Yield: 51,8 g (85%).

Analysis: $C_{21}H_{30}N_2O_7$ (422.48): Calculated: C, 59.70%; H, 7.16%; N, 6.63%. Found: C, 59.31%; H, 7.22%; N, 6.45%.

EXAMPLE 42

N-[ε-(O-acetyl-lactyl)-α-(3,5-diacetamido-2,4,6-triiodobenzoyl)]-L-lysine ethyl ester (XL)

42.6 g (0.047 Mol) N-[ε-benzyloxycarbonyl-α-(3,5-diacetamido-2,4,6-triiodobenzoyl)]-L-lysine ethyl ester were suspended in 235 ml acetic acid and reacts with 50 ml 33% hydrogen bromide in acetic acid. The solution is added dropwise to 1.5 l ether. After 2 hours at room temperature, the precipitate is filtered off and washed with ether. The hydrobromide is dissolved in 250 ml N,N-dimethylformamide, reacts with 13,8 ml (0,1 Mol) triethylamine, stirred over night at room temperature, the triethylammonium bromide is filtered and the solvent is distilled off. The residue (about 35 g) is dissolved in 175 ml N,N-dimethylformamide, reacts with 7,8 g (0.060 Mol) O-acetyl-lactyl chloride and 13.8 ml (0.1 Mol) triethylamine, stirred for 24 hours at room temperature, the triethylammonium chloride is filtered off, the N,N-dimethylformamide is distilled off and the oil residue is mixed with ethyl acetate. The substance crystallizes. It is filtered off, washed with petroleum ether, washed with water and dried.

Yield: 30,4 g (75%).

Analysis: $C_{24}H_{31}N_4O_8I_3$ (884.24): Calculated: C, 32.60%; H, 3.53%; N, 6.34%. Found: C, 32.66%; H, 3.64%; N, 6.16%.

EXAMPLE 43

N-[α-(O-acetyl-lactyl)-ε-(3,5-diacetamido-2,4,6-triiodobenzoyl)]-L-lysine ethyl ester (XXXIX)

51.8 g (0.12 Mol) N-[ε-benzyloxycarbonyl-α-(O-acetyl-lactyl)]-L-lysine ethyl ester is dissolved in 150 ml acetic acid and 120 ml 33% hydrogen bromide in acetic acid added thereto dropwise under stirring. After 2 hours at room temperature the solution is added to 1.5 l ether dropwise, decanted after a few hours, the oil is dissolved in 500 ml N,N-dimethylformamide, reacts with 35 ml (0.25 Mol) triethylamine, stirred overnight, the triethyl ammonium bromide is filtered off and the solvent is distilled under vacuum. The residue is dissolved in 450 ml N,N-dimethylformamide, 75 g (0.12 Mol) 3,5-diacetamido-2,4,6-triiodobenzoyl chloride are added and thereafter reacts with 35 ml (0.25 Mol) triethylamine. The reaction runs for 24 hours at room temperature. The triethylammonium chloride is filtered off the next day, the solvent is distilled off under vacuum. The residue is mixed with ethyl acetate. The crystallized substance is filtered off, washed with petroleum ether dried, washed with water, 1N hydrochloride acid, water, saturated sodium bicarbonate solution and water, dried. Yield: 45 g (42%).

Analysis: $C_{24}H_{31}N_4O_8I_3$ (884.24): Calculated: C, 32.60%; H, 3.53%; N, 6.34%. Found: C, 32.58%; H, 3.15%; N, 6.17%.

The configuration of the α-amino acid moiety may be arbitrary. The type of amino acid residue influences to a degree the solubility of the compound of the invention in water. For example, the compounds (II), (IX), (X), and (XI) are all very soluble (over 100%) while the compounds (III) and (VIII) are soluble (up to 50%) and the compounds (IV), (V), (XI) and (XII) are moderately soluble (up to 20%).

Therefore, water solubility of the compounds of the invention is not only dependent on the number of hydroxy groups, but also from the type of the N-alkylation of the amino acid moiety.

The degree of water solubility does not affect the value or usefulness of the compounds (I) of the invention. Indeed, the compounds II, IX, X and XI are superior in respect to solubility. The primary requirements for a useful X-ray contrast agent are (a) optimum of general and local compatibility;
(b) low toxicity;
(c) minimum viscosity;
(d) sufficient solubility; and
(e) low osmotic pressure.

These properties are better obtained with nonionic contrast agents than with ionized contrast agents.

Therefore, we should point out the excellent solubility in water, the relative very good viscosity data, as well as the very low toxicity of the compounds of the invention. The osmotic pressure in nonionized contrast agents is lower than with comparable ionic formulas, due to their structure.

The derivatives of compounds (I) of the invention which show a good solubility in water generally show viscosity values which, as can be expected, are dependent from the number and position of the hydroxy groups, as well as from the configuration of the amino acid residue. Representative compounds of the invention are shown in the Table 1, with their viscosity values.

TABLE 1

Viscosity data in dependency from the type of amino acid and the concentration of the preparation.

| Concentration (mg J/ml) | Viscosity (cP) | | | | | | | |
|---|---|---|---|---|---|---|---|---|
| | 20° C. | | | | 37° C. | | | |
| | Compounds | | | | | | | |
| | II | VIII | IX | X | II | VIII | IX | X |
| 100 | 2.16 | 2.13 | 2.90 | — | 1.48 | 1.84 | 1.84 | — |
| 150 | 3.50 | 3.11 | 5.15 | — | 2.22 | 1.95 | 3.04 | — |
| 200 | 5.74 | 5.15 | 11.14 | 10.65 | 3.32 | 3.04 | 6.06 | 5.84 |
| 250 | 10.84 | 9.43 | 33.58 | 25.38 | 6.20 | 5.16 | 15.96 | 12.23 |
| 300 | 18.88 | 20.05 | 88.85 | — | 9.22 | 9.71 | 35.41 | — |

Aqueous solutions of the novel nonionic derivatives of the 3,5-diacetamido-2,4,6-triiodobenzoic acid (I) are thermally stable, so that a heat sterilization does not impair their use, as shown in the Table 2, below.

TABLE 2

Behaviour of a 67,9% aq. solution of (II) at different temperatures and times.

| Time min. | Temp. °C. | pH | Iodide mg J/100 ml | Color |
|---|---|---|---|---|
| Base solution | | 7.85 | 1.78 | colorless |
| 30 | 110 | 7.85 | 2.63 | colorless |
| 60 | 110 | 7.75 | 3.72 | colorless |
| 30 | 120 | 7.80 | 3.73 | colorless |

In relationship to the ionized Na-, N-methyl-glucamine or lysine salts of the 3,5-diacetamido-2,4,6-triiodobenzoic acid, the derivative compounds (I) of the invention are characterized by lower osmotic pressure, so that their general and local compatibility is improved.

Toxicity studies show the low toxicity of the compounds (II), as can be seen from Table 3, below.

TABLE 3

$LD_{50}$ in mouse, i.v. (14 days after application) of solution with a content of 300 mg J/ml.

| Substance | $LD_{50}$ (g/kg) |
|---|---|
| sodium-meglumine-diatrizoate | 12–14 |
| lysine-diatrizoate | 14–18 |
| diatrizoyl-sarcosine-N—methyl glucamide (II) | 36 |

What is claimed:

1. N,N-[(3,5-diacetamido-2,4,6-triiodbenzoyl)-aminoacyl]-N-methylglucamide of the formula:

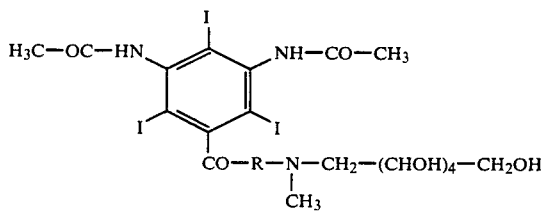

(I)

where R denotes an amino acid residue, wherein the amino acid is selected from the group consisting of alanine, β-alanine, sarcosine, amino butyric acid, leucine, serine, aspartic acid and glutamic acid.

2. The compound of claim 1 which is N,N-[(3,5-diacetamido-2,4,6-triiodobenzoyl)-sarcosine]-N-methyl glucamide (II).

3. The compound of claim 1 which is N,N-[(3,5-diacetamido-2,4,6-triiodobenzoyl)-L-alanine]-N-methyl glucamide (III).

4. The compound of claim 1 which is N,N-[(3,5-diacetamido-2,4,6-triiodobenzoyl)-β-alanine]-N-methyl glucamide (IV).

5. The compound of claim 1 which is N,N-[(3,5-diacetamido-2,4,6-triiodobenzoyl)-γ-amino butyric acid]-N-methyl glucamide (V).

6. The compound of claim 1 which is N,N-[(3,5-diacetamido-2,4,6-triiodobenzoyl)-L-leucine]-N-methyl glucamide (VI).

7. The compound of claim 1 which is N,N-[(3,5-diacetamido-2,4,6-triiodobenzoyl)-L-phenylalanine]-N-methyl glucamide (VII).

8. The compound of claim 1 which is N,N-[(3,5-diacetamido-2,4,6-triiodobenzoyl)-L-serine]-N-methyl glucamide (VIII).

9. The compound of claim 1 which is N,N-[α-lactyl-ε-(3,5-diacetamido-2,4,6-triiodobenzoyl)-lysine]-N-methyl glucamide (XII).

10. The compound of claim 1 which is N,N-[ε-lactyl-α-(3,5-diacetamido-2,4,6-triiodobenzoyl)-lysine]-N-methyl glucamide (XIII).

* * * * *